United States Patent
Combrink

(10) Patent No.: US 7,698,877 B2
(45) Date of Patent: Apr. 20, 2010

(54) PACKAGING MACHINE AND DISCHARGING DEVICE FOR A PACKAGING MACHINE

(75) Inventor: Alois Combrink, Oelde (DE)

(73) Assignee: Haver & Boecker OHG, Oelde (DE)

( * ) Notice: Subject to any disclaimer, the term of this patent is extended or adjusted under 35 U.S.C. 154(b) by 173 days.

(21) Appl. No.: 12/142,149

(22) Filed: Jun. 19, 2008

(65) Prior Publication Data
US 2008/0318750 A1    Dec. 25, 2008

(30) Foreign Application Priority Data
Jun. 22, 2007   (DE) .................. 10 2007 029 278

(51) Int. Cl.
*B65B 5/00*        (2006.01)
(52) U.S. Cl. .................. 53/467; 53/167; 53/284.7; 53/502; 73/865.8; 73/862.541; 177/50
(58) Field of Classification Search .................. 53/467, 53/52, 58, 167, 469, 502; 73/865.8, 49.2, 73/49.3, 862.541, 52, 580; 177/45, 50, 145, 177/245, DIG. 11
See application file for complete search history.

(56) References Cited

U.S. PATENT DOCUMENTS

| | | | | |
|---|---|---|---|---|
| 3,977,483 | A * | 8/1976 | Greanias .................. 177/1 |
| 4,148,213 | A * | 4/1979 | Prakken .................. 73/45.4 |
| 4,231,439 | A * | 11/1980 | Hall et al. .................. 177/25.14 |
| 4,649,740 | A * | 3/1987 | Franklin .................. 73/49.3 |
| 5,308,930 | A * | 5/1994 | Tokutu et al. .................. 177/25.13 |
| 5,507,177 | A * | 4/1996 | Focke .................. 73/49.3 |
| 5,531,101 | A * | 7/1996 | Fenlon .................. 73/49.3 |
| 5,542,288 | A * | 8/1996 | Fenlon .................. 73/49.3 |
| 5,786,530 | A * | 7/1998 | Fenlon .................. 73/49.3 |
| 5,832,700 | A * | 11/1998 | Kammler et al. .................. 53/502 |
| 5,881,532 | A * | 3/1999 | Kitagawa .................. 53/54 |
| 5,918,270 | A * | 6/1999 | Heuft .................. 73/45.4 |
| 6,094,888 | A * | 8/2000 | Pazdernik et al. .................. 53/436 |
| 6,105,419 | A * | 8/2000 | Michels et al. .................. 73/49.3 |
| 6,474,141 | B1 * | 11/2002 | Takaoka et al. .................. 73/49.3 |
| 6,568,247 | B2 * | 5/2003 | Taylor .................. 73/49.3 |
| 6,711,874 | B1 | 3/2004 | Nakagawa et al. |
| 7,231,749 | B2 * | 6/2007 | Garceau et al. .................. 53/403 |
| 7,475,590 | B2 * | 1/2009 | Yokota et al. .................. 73/45.4 |

(Continued)

FOREIGN PATENT DOCUMENTS

DE        938418        1/1956

(Continued)

*Primary Examiner*—Thanh K Truong
(74) *Attorney, Agent, or Firm*—Pearne & Gordon LLP

(57) ABSTRACT

Packaging machine and discharging device for a packaging machine, and a method for filling bags by means of a packaging machine, wherein a bag to be filled is filled by means of a filling element and the filled bags are taken off by means of a bag take-off device and transferred to a discharging device. The discharging device comprises a conveying device for conveying off the bags filled with bulk goods, wherein at least one monitoring device for monitoring the tightness of the filled bags is provided which is associated with the conveying device. Said monitoring device comprises a weight sensor which captures a measure for the bulk material escaping from a bag to determine a parameter for the bag leakiness.

15 Claims, 3 Drawing Sheets

U.S. PATENT DOCUMENTS

Figure 1:
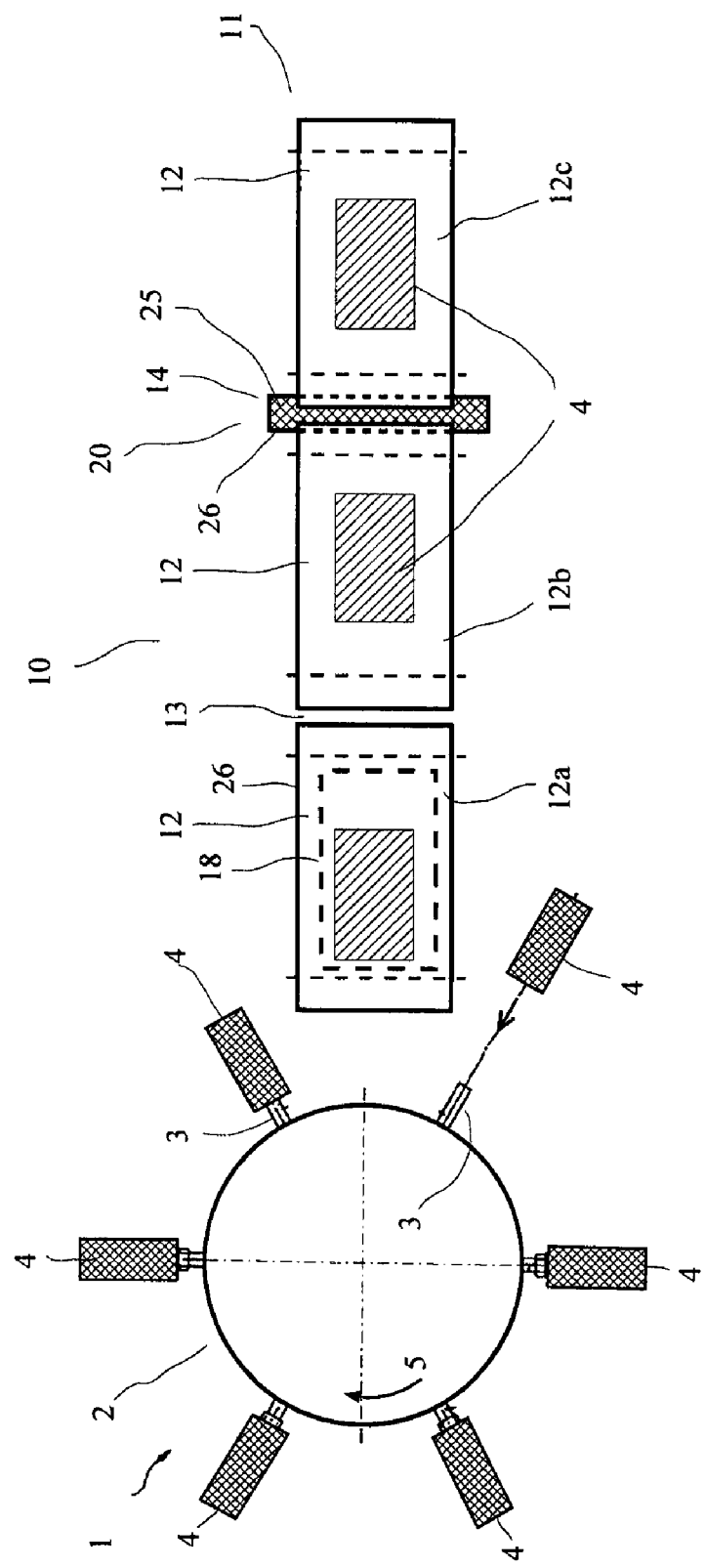

2003/0019728 A1* 1/2003 Kitagawa et al. ............ 198/604
2008/0115566 A1* 5/2008 Van Rootselaar ............ 73/49.3

FOREIGN PATENT DOCUMENTS

| | | | |
|---|---|---|---|
| DE | 2045713 A | 12/1971 |
| DE | 19857476 A1 | 6/2000 |
| DE | 102005030693 A1 | 1/2007 |
| DE | 102005057864 A1 | 6/2007 |
| EP | 1050469 A1 | 11/2000 |

* cited by examiner

PACKAGING MACHINE AND DISCHARGING DEVICE FOR A PACKAGING MACHINE

The invention relates to a discharging device for a packaging machine, and to a packaging machine equipped with such a discharging device and to a method for filling loose bulk goods into bags.

Packaging machines according to the invention may be provided for filling loose bulk goods into so-called open bags where the filling element extends into the open bag from above. In these cases virtually the entire bag cross-section can be employed as the filling cross-section to thus achieve a high filling speed.

Furthermore the invention is in particular also suitable for filling so-called valve bags wherein the package is provided with a tab-like section at which a bag valve is provided. For filling, the bag is placed on the filling element configured as a filling spout through which filling of the bag with the bulk goods to be filled takes place. Between the filling element and the bag valve, a filling collar may be provided which is inflated during filling to seal the bag against the ambience.

After filling, all of the methods may provide for sealing the bags tight. In filling open bags the filling opening is e.g. closed by welding to prevent the filled bulk goods from escaping. In the case of valve bags, a so-called self-sealing valve may be provided in the bag valve to automatically, substantially prevent any filled bulk goods from escaping. Since their sealing properties are no longer satisfactory in recent times, up to date installations may provide a closing unit also for valve bags for gluing or welding the bag valves shut to prevent filled material from escaping.

In every filling machine, however, e.g. due to an incorrect filling operation or faulty bag material, individual bags may be leaking. For example the bags discharged from a rotary packaging machine equipped with multiple filling elements may burst as they hit the discharging device, in particular if the bag material employed has some weak spots. There may occur large-area ruptures; or else a small, fine tear may appear through which only comparatively small quantities of the filled bulk material escape but it may be assumed that during the further transport and further handling of the filled bag, more bulk material will escape from the bag. The escaping bulk material will then contaminate the pallet on which the bags are stacked, the transport vehicle, or the sales floor in the shop.

These days the market is increasingly quality-conscious and also demands reliably tight bags to avoid contamination of the ambience and e.g. in the shop. The customers also expect clean bags. Therefore there is the requirement for packaging machines to check the quality of bags and bag closing means to allow to reliably pull out insufficiently closed bags. The reason is evident since for example in the case of valve bags only one bag needs to be not quite closed to contaminate an entire pallet. This problem is still more serious in the case of open bags manufactured and handled for example in a form-fill-seal machine since a defective bag may even cause a filled pallet to turn over or at least it may require the manual labor of removing a bag from the pallet.

A number of methods have become known for checking bags for leak tightness and for recognizing leakiness in bags. For example photoelectric methods have become known in which a photoelectric sensor detects any material trickling out of a bag to thus determine leaking bags. While this method allows checking for bag tightness in absolutely dust free areas, it has been found to be unsuitable in particular in filling dusting materials since during or at the end of the filling operation, small, minute quantities of the bulk material to be filled will always be emitted to the ambience, thus resulting in a certain dust content in the air. In this way, when bagging dusting materials, bags may be recognized as not tight although they are sealed tight, or non-tight bags may not be recognized as not tight since the threshold for detecting a non-tight bag has been set at a less than optimal level. Furthermore, dust settling on the photo cell may cause still more incorrect measurement results. On the whole, this method is thus not suitable for checking the tightness of bags when bagging dusting materials.

Furthermore, methods for checking bag tightness have become known in which colorimetry is employed for detecting color changes where e.g. in bagging a product white in color, e.g. gypsum, color changes are being detected on black belts disposed on the bags. As the black belt had assumed a specified gray color, a leakiness of the bag was concluded. What is a problem in this known method is the setting of the threshold since any ambience dust that may be present may cause the belts to not always be deep black such that this method has again be found to be unsuitable. Also, this method is only suitable for specific combinations of colors of the package versus the bagged material.

Another known method is based on the filled, tight sealed bags being conveyed beneath a pressing conveyor belt in such a way that part of the length or width of the bag is weighted while another part remains unweighted. In the case of a bag sealed tight any air still present in the product will generate an air bubble in the unweighted bag part, resulting in an air bubble which e.g. optical detectors can detect. Since the air content in the bag is dependent on the filled material and other conditions and it may vary from case to case, this method has again not achieved any satisfactory accuracy.

On the whole it can be found that in bagging powdery materials, none of the known methods provides for a satisfactory checking for bag tightness.

It is therefore the object of the present invention to provide an apparatus and a method which allow a reliable and highly accurate checking for bag tightness after filling bags even in the case of dusting or powdery products.

This object is fulfilled by a device having the features of claim 1, by a packaging machine having the features of claim 11, and by the methods having the features of claims 14 and 15. Preferred configurations are the subjects of the subclaims. Further advantages and characteristics can be taken from the general description and the description of an embodiment.

The discharging device according to the invention for a packaging machine is equipped with a conveying device for conveying off the bags filled e.g. with dusting or powdery bulk materials. At least one monitoring device for monitoring the tightness of the filled bags is provided which is associated with the conveying device. Said monitoring device comprises at least one weight sensor for directly capturing any bulk material escaping from a bag to obtain a parameter for the bag tightness when bagging dusting materials.

The discharging device according to the invention offers considerable advantages. The discharging device does not only convey the filled bags off a packaging machine but at the same time checks the bags for tightness wherein statistical evaluations allow an analysis of the packing process.

Employing a weight sensor allows reliably checking bags for tightness, independently of the product to be bagged and the ambient conditions.

Directly measuring any escaped bulk materials will in particular achieve high accuracy such that even minor leakiness may be detected at a high degree of reliability. If, however, the escaped bulk material is not directly measured but the bag weight is measured and an escaped proportion computed therefrom, considerable uncertainties in determining tightness will ensue.

For example in the case that only a mass of e.g. 10 or 50 grams has escaped from the bag, the proportion in the case of a bag weight of 25 or 50 kg is minor but it may still lead to considerable contamination of the ambience and the outer bag wall. For example in the case of measuring the entire bag weight while reliably detecting this amount of underweight, the bag weight must be determined at a very high accuracy.

There is also the quite considerable difficulty that the bag weight at discharge is only determined at a specified accuracy since small amounts may for example escape from the valve of a valve bag. These inaccuracies add up. On the whole there will result a considerable uncertainty when checking bag tightness if said bag tightness is intended to be determined by way of measuring the total weight of the filled bag. The direct measuring according to the invention of escaped bulk material avoids these disadvantages, allowing high accuracy.

In a particularly preferred specific embodiment of the invention the discharging device comprises at least one collecting unit to collect any bulk material escaping from a non-tight bag. This specific embodiment offers particular advantages since checking for bag tightness does not require to weigh the entire bag since the bag weights and the permissible weight tolerances of a package are considerably larger than can be expected in the case of minor leakiness. Therefore the conventional accuracy and the weighing capacity of a bag check weigher as it is employed for detecting underweight bags are not suitable to reliably determine such a value. Thus, in order to detect any underweight, only the bulk material escaped and collected in the collecting unit is weighed so as to achieve a particularly high accuracy and reliability of checking for bag tightness. For example if 20 g of the material to be filled escape from a small tear in the bag, this is a very small proportion in the case of a total weight of e.g. 50 kg, such that this difference of the total weight might possibly not be regarded as significant. If, however, a collecting unit is loaded with 20 g bulk material, the effective weight has increased quite considerably.

In a preferred embodiment of the invention a weighting unit or weighting device is provided which serves for weighting the filled bags at the discharging device. In this way the bags are submitted to a weight for the filled product to escape from any tears or holes or the like which may be present. The escaping product or at least a considerable proportion of the escaping product is then collected in the collecting unit and detected to thus allow capturing a direct measure of leakiness.

It is particularly preferred for the or at least one monitoring device to be positioned downstream of the weighting device.

Advantageous specific embodiments provide for multiple conveyor units to be disposed in series which are in particular disposed separately from one another. This allows that any product falling onto a conveyor unit which has escaped from a bag is not conveyed to the next discharging unit such that the individual conveyor units are decoupled from one another.

A monitoring device is preferably associated with a gap between two conveying units. The monitoring device may in particular be provided beneath the gap or it may be connected with the gap by means of a guide passage or the like such that any material falling into the gap between the conveying units is led to the monitoring device.

Preferably a first conveying unit is provided onto which the bags to be conveyed off are deposited or dumped after the checking operation. Therefore it is possible that a certain quantity of material to be bagged falls onto said first conveying unit in particular when filling valve bags since as a valve bag is taken off a certain quantity of product tends to be still present in the region of the valve. Most of it is ejected at impact with the first conveying unit of the discharging belt such that any material present in this place is not an actual indication of a defective bag.

However, when the filled bag is transferred from the first conveying unit to a second or to a specified conveying unit, any material escaping at said second or specified conveying unit is an indication of bag leakiness. It is therefore preferred for the monitoring device or a monitoring device to be provided between the specified and a subsequent conveying unit. Preferably the weighting device is provided as a vibrating section or the like transmitting vibrating movements to the filled bag to equalize the product level in the bag and to provoke the escape of material through any existing tears by way of the weight applied to the bag.

Another configuration may provide, instead of or in addition to a vibrating section, a bag pressing device configured for example in the shape of a flattening and/or pressing section and in which the bag is compressed to obtain specified package dimensions and/or to provoke the escape of material from the bag. Any material escaping from the bag is collected in the collecting unit or units and a measure of the bulk material escaped from the bag is captured by means of the weight sensor to obtain a parameter for the bag tightness.

It is also possible for a conveying unit to comprise a belt inlet to give the bag a specified shape e.g. in the vertical direction.

Preferred specific embodiments provide for multiple conveying units to be configured as conveyor belts. The monitoring device is preferably disposed at the abutting ends of two adjacent conveyor belts or associated with the abutting belt ends.

In all of the above described configurations and specific embodiments of the invention the weight sensor is preferably equipped with a commercial strain measuring technology. In this way a reliable and high resolution weight capturing is possible. Since in capturing the weight of a collecting unit the weight sensor may be configured such that a maximum of 10%, 20% or 30% of the bag weight can be captured, this allows a particularly high-resolution measuring of any material escaping from a bag. Also, the weight sensor may comprise at least one piezoelectric element.

Preferred specific embodiment provide for at least one collecting unit to be configured as a collecting tray which when employed in packaging machines for filling open bags preferably extends over the entire width of the conveying unit such that any bulk material falling into the gap between two conveying units or conveyed into the gap by way of the conveying movement of the conveying unit, is collected by the collecting tray and detected over the entire width.

In preferred specific embodiments the collecting unit is configured rotatable or pivotable to allow throwing off the collected material by way of a rotating or pivotal movement. This allows a reliable and continuous operation particularly easily.

In other configurations or additionally, a suction apparatus may be provided to draw off any collected material from the collecting unit as required.

In preferred specific embodiments the collecting unit comprises a double or multiple-sided collecting tray wherein a rotation of the collecting unit by a suitable angle brings the next collecting tray into the operating position, while any material collected in the collecting tray previously employed for collecting the bulk material is discarded such that said tray can then be employed again.

In all of the configurations the monitoring device may comprise a collecting hopper for collecting any material trickling down e.g. over the width of the conveying unit or over the width of the gap between two conveying units, and feeding it to the collecting unit.

In another preferred specific embodiment a baffle plate is provided disposed e.g. at an angle relative to the horizontal for any material trickling down to fall on. The momentum generated at impact on the baffle plate is evaluated, and a measure of the weight is determined to thus allow determining a parameter for the tightness of the bag when employing a baffle plate.

The packaging machine according to the invention serves for filling bulk materials into bags and in particular for filling powdery and dusting materials into bags, comprising at least one filling element for filling the bag to be filled. Furthermore, at least one bag discharge device for taking off the filled bags and for transferring said bags to a discharging device may be provided. The discharging device comprises a conveying device by means of which the filled bags are conveyed off. Furthermore at least one monitoring device is provided for monitoring the tightness of the filled bags which is in particular associated with the conveying device. Said monitoring device comprises at least one weight sensor for capturing a measure for the bulk material escaping from a bag to determine a parameter for the bag leakiness.

The packaging machine according to the invention also offers a plurality of advantages. The packaging machine according to the present invention allows filling all kinds of bulk materials including powdery and dusting products, wherein monitoring the tightness of the bags allows to realize an improved cleanliness in the ambience and in the further handling. Furthermore the bags conveyed off have an improved bag quality on average because faulty bags can be detected and thus discarded.

Preferably the packaging machine is equipped with a plurality of filling elements and it may in particular be configured to be rotary.

The packaging machine may be suitable and specified for filling bulk goods into valve bags or, in other configurations, configured for filling bulk goods into open bags. When filling open bags the packaging machine according to the invention may manufacture, fill and then close the bags as required from a continuous sheet of tubular film.

It is preferred in all of the cases to have a bag closing unit at the packaging machine for gluing or welding shut the filling ends of open bags and for closing the valves of valve bags.

Preferred specific embodiments of the packaging machine according to the invention provide for any detected non-tight bags to be pulled out.

When filling a plurality of bags, a statistical analysis may be performed and in dependence on the parameters determined successively, at least one filling parameter and/or at least one closing parameter may be adapted. For example if it is determined that a larger quantity of bags is non-tight than could be expected in typical conditions, the filling pressure applied in filling may be reduced to avoid further rupturing of bags. Or else, closing parameters such as the welding time or the welding intensity may be varied to prevent defects in closing the bags.

In the method according to the invention a bag is filled e.g. with powdery or dusting bulk goods and then it is closed. The filled bag is transferred to a discharging device and any bulk goods escaping from the filled bag are collected and weighed to capture a measure of the bulk goods escaped from the bag. In this way a parameter for the tightness of the bag may be determined. Furthermore, any bags detected as being non-tight are preferably pulled out.

The escaped material may be collected in a collecting tray or the like which is weighed periodically or continuously. The collecting tray or collecting unit may be emptied out after each bag or else as a predetermined weight is reached. In the case that detecting is provided only for the relative weight increase, emptying out is not required each time which increases the throughput capacity.

In another configuration of the inventive method of filling bulk goods in bags, a bag is filled with bulk goods and then closed. The filled bag is transferred to a discharging device and any bulk goods escaping from the bag are transferred to a baffle plate at least in part. The momentum generated at impact is captured and a parameter for the tightness of the bag is determined. The captured measured values may be averaged and/or added up.

Specific embodiments and configurations of the method according to the invention and the packaging machine according to the invention employ a discharging device described above.

Further advantages and applications of the present invention ensue from the embodiments which will now be described with reference to the attached Figures.

Figure 2:
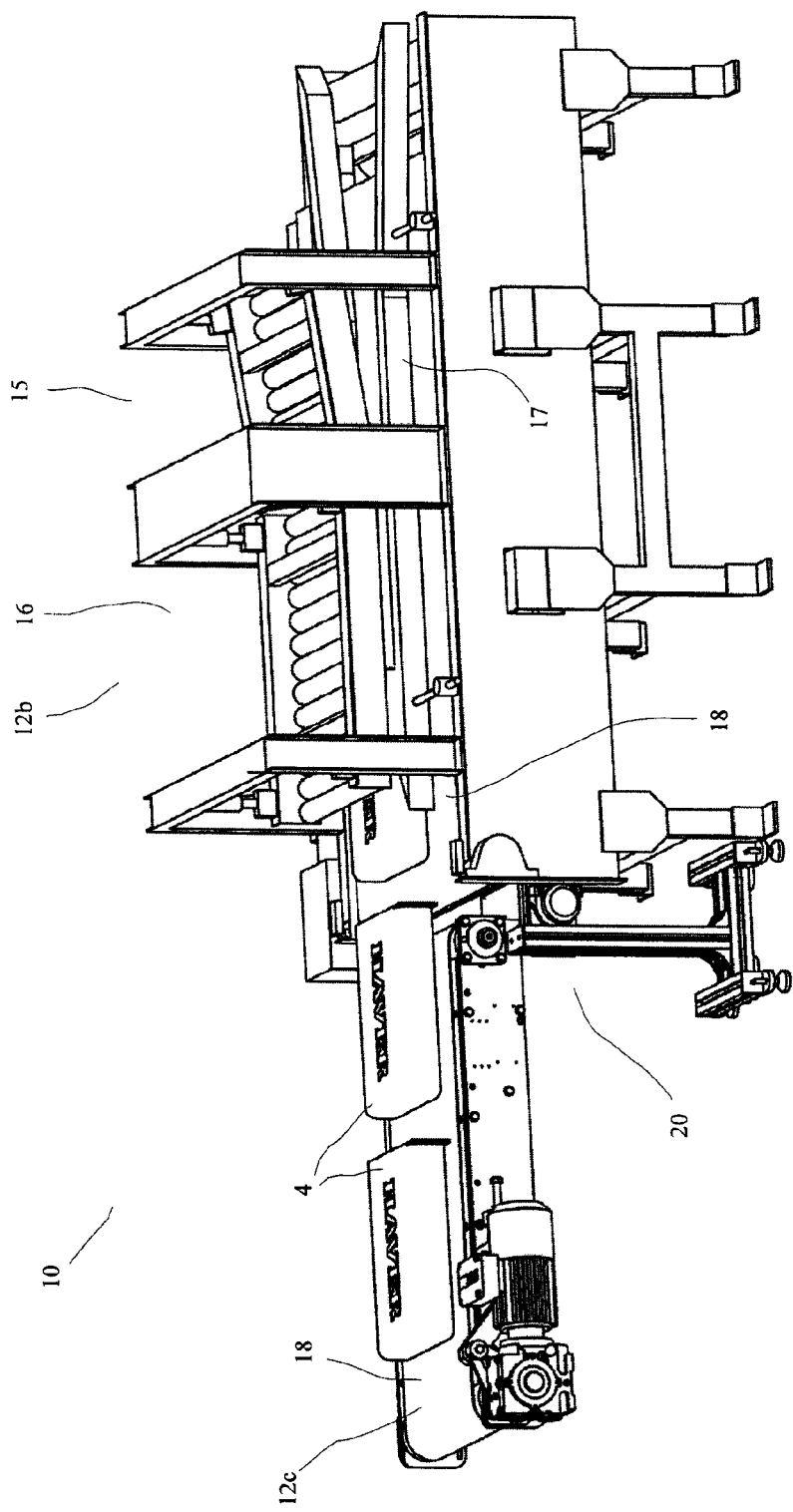
Figure 3:
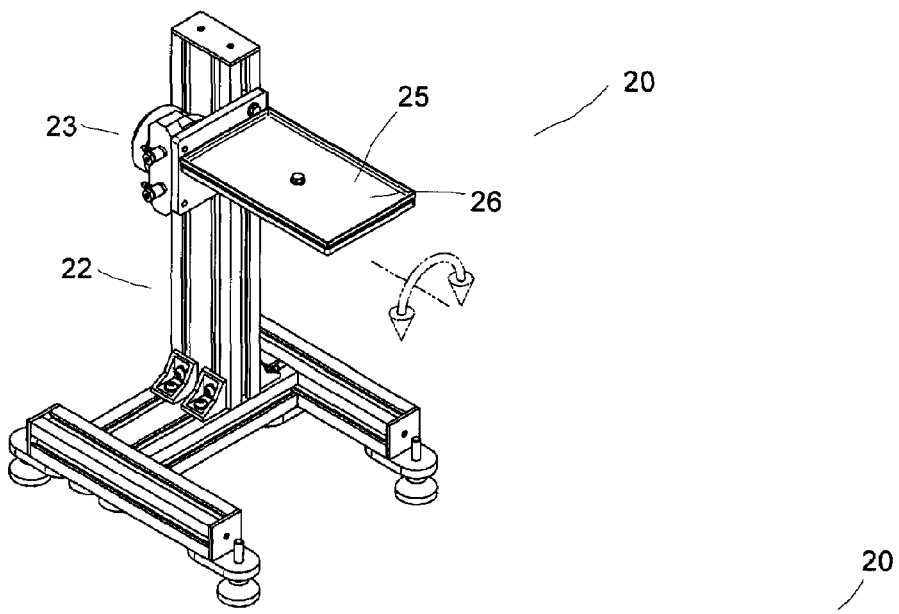
Figure 4:
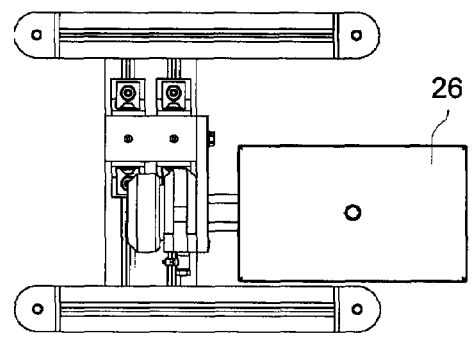
Figure 5:
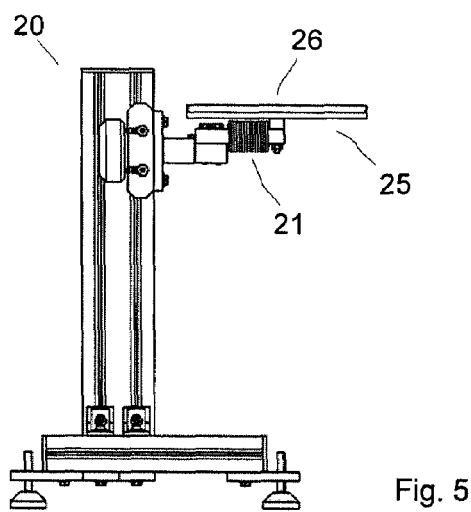
Figure 6:
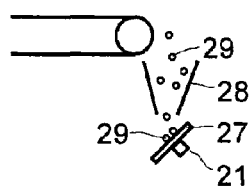

These show in:

FIG. 1 a top view of a packaging machine according to the invention with a discharging device according to the invention in a simplistic view;

FIG. 2 a perspective view of an inventive discharging device;

FIG. 3 a perspective view of the monitoring device according to FIG. 2;

FIG. 4 a top view of the monitoring device according to FIG. 3;

FIG. 5 a side view of the monitoring device according to FIG. 3;

FIG. 6 a simplistic side view of another embodiment in which a baffle plate is employed in the monitoring device.

FIG. 1 shows a simplistic top view of an inventive packaging machine 1 which is equipped with an inventive discharging device 10. Although the packaging machine 1 in the present example is employed for filling valve bags 4, the inventive packaging machine may be provided in other configurations for filling open bags which do not have a valve but are filled substantially over the entire cross-section.

The packaging machine 1 comprises a housing or a framework 2 and it is configured as a rotary packaging machine, comprising six filling spouts 3 in the present example. Other configurations may provide for a different number of filling elements or filling spouts 3. More or less filling elements may be provided; for example 8, 10, 12 or 16 filling elements may be disposed at the packaging machine according to the invention.

Before filling the bags 4, the bags 4 are pushed or shot onto the filling spouts 3 by means of a pushing device (not shown). Or else, manual placement is possible.

The packaging machine 1 rotates in the rotational direction 5 while the bags 4 are filled one by one with the bulk goods 29 to be bagged. The packaging machine 1 can in particular be employed for filling dusting and powdery bulk goods 29. For example, all kinds of loose bulk construction materials or powdery chemical products etc. may be bagged.

While the packaging machine 1 rotates, the bags 4 are filled one by one while their weight is established continuously or at short intervals and compared against the intended filled weight. As a predetermined weight is reached, the filling process is decelerated in that the coarse filling phase is changed to the fine filling phase in which the bulk goods 29 to be filled are transferred into the bag 4 in smaller quantities per unit time so as to avoid pressure peaks during filling and to obtain the precise intended filled weight.

After achieving the target weight the filling process is stopped, the filled bag 4 is taken off the filling spout 3, and then the bag valve is closed in a closing device (not shown). Closing may be performed by way of welding or by adding adhesive.

The filled, closed bag 4 is then mechanically or manually thrown or placed on the discharging device 10 where it is transferred to the conveying unit 12a of the conveying device 11. The impact of the filled bag 4 on one of the conveying units 12 of the conveying device 11 in particular causes a portion of any bulk goods which may still be present in the region of the bag valve to escape and then to be conveyed further on the conveyor belt 18.

The first conveying unit 12a is followed by a second or a further conveying unit 12b, with an air gap 13 remaining between the conveying units 12a and 12b for the bulk goods escaped e.g. from the bag valve at impact on the conveying unit 12a and lying on the conveyor belt 18, to fall in. By means of the transition of the bags 4 from the first conveying unit 12a to the second conveying unit 12b it is ensured that no more bulk goods are present on what is presently the second conveying unit 12b.

The second or a further conveying unit 12b is provided with the weighting device 15 indicated only schematically which for example transmits a vibrating movement to the filled bag 4 from below. In this way the filled bag 4 is weighted such that bulk goods 29 will escape from the bag 4 through a tear which may be present in the bag coat and fall onto the conveyor belt 12a.

The end of the second conveying unit 12b is followed by another gap 14 for any bulk goods 29 escaping during the weighting process to fall in. Beneath the gap 14 a monitoring device 20 is provided which presently comprises a collecting unit 25 configured as a collecting tray 26. In this way any material or bulk goods 29 escaping during the vibrating movement of the weighting device 15 is collected in the collecting tray 26. The monitoring device 20 further preferably comprises a weight sensor 21 (see e.g. FIG. 6) equipped with strain measuring technology or with a piezoelectric sensor, so as to capture the weight of the escaped and collected bulk goods 29.

In this way it can be determined for each bag 4 whether and how much material escapes during weighting of the bag 4 to thus allow to capture a measure for any bulk goods 29 escaped from the bag 4 from which a parameter for the bag tightness can be derived.

The parameter is employed for deciding whether the bag 4 is graded high quality and can be handled further or whether the bag 4 is graded low quality and will be withdrawn from the further loading process.

FIG. 2 illustrates a perspective view of the discharging device 10 at which a monitoring device 20 is provided.

The bags 4 which in the present illustration according to FIG. 2 arrive at the end of the discharging device 20 on the right are conveyed further by means of the conveying units 12.

The second conveying unit 12b comprises a weighting device 15 which is presently configured as a bag pressing device 16 and comprises a flattening and pressing section. Said bag pressing device 16 comprises a belt inlet 17 by means of which the bags 4 are given the intended shape. At the same time the weighting device 15 applies a pressure on the bags 4 for any filled bulk goods 29 to escape and to fall onto the conveyor belt 18, in the case of torn or defective bags 4.

A gap 14 is provided between the conveying unit 12b and the conveying unit 12c through which any bulk goods 29 accumulated on the conveyor belt 18 will fall down. There it is gathered in the collecting tray 26 of the monitoring device 20 and its weight is captured so as to allow to decide for each bag 4 whether the bag tightness is satisfactory.

The FIGS. 3, 4 and 5 are enlargements of the monitoring device 20. FIG. 3 shows a perspective illustration of the monitoring device 20 which presently is provided with a collecting unit 25 configured as a collecting tray 26. The collecting unit 25 is disposed to be height-adjustable by means of the framework 22, comprising a tilting unit 23 for overturning the collecting tray 26 such that any material or bulk goods 29 accumulated in the collecting tray 26 will fall down.

In specific configurations the collecting tray 26 may be designed double-sided such that after a rotation of 180 degrees the collecting tray 26 that was previously below now collects any material trickling down from above, such that after every rotation of 180 degrees the collecting tray is again ready for operation.

It is possible to empty out the collecting tray 26 each time a bag 4 is removed to thus obtain the largest possible resolution. Or else it is possible to empty out the collecting tray 26 only as a specified collected weight is reached. Then the difference per each bag 4 is determined to derive the parameter for the bag tightness.

FIG. 6 illustrates another embodiment in which the collecting tray 26 is replaced by a baffle plate 27 with the weight sensor 21 provided beneath. Then the mode of operation is that, as bulk goods 29 trickling down hit on the baffle plate 27, a pulse is triggered which is captured and processed by the evaluation unit (not illustrated), such that adding the quantity and level of the pulses allows to derive the measure of the bulk goods 29 trickling down, which again allows to compute a parameter for the bag tightness.

FIG. 6 furthermore indicates a receiving hopper 28 for bundling the material or bulk goods 29 trickling down onto the baffle plate 27. This hopper 28 may be employed when a collecting tray 26 is used for example to delimit the size of the collecting tray 26 used.

LIST OF REFERENCE NUMBERS

1 packaging machine
2 housing
3 filling element
4 bag
5 direction of rotation
10 discharging device
11 conveying device
12 conveying unit
12a conveying unit
12b conveying unit
12c conveying unit
13 gap
14 gap
15 weighting device
16 bag pressing device
17 belt inlet
18 conveyor belt
20 monitoring device
21 weight sensor
22 framework
23 tilting unit
25 collecting unit
26 collecting tray 27 baffle plate
28 collecting hopper
29 bulk goods

The invention claimed is:

1. A discharging device (10) for a packaging machine (1), comprising a conveying device (11) for conveying off bags (4) filled with bulk goods, wherein at least one monitoring device (20) for monitoring the tightness of the filled bags (4) is provided which is associated with the conveying device (11), characterized in that the monitoring device (20) comprises at least one weight sensor (21) which directly captures the bulk material (29) escaping from a bag (4) to obtain a parameter for the bag tightness.

2. The discharging device (10) according to claim 1, wherein the monitoring device (20) comprises a collecting unit (25) having at least one collecting tray (26).

3. The discharging device (10) according to claim 1, wherein the conveying device (11) comprises at least one weighting device (15), wherein in particular the weighting device (15) is series-connected to be followed by the monitoring device (20).

4. The discharging device (10) according to claim 1, wherein the conveying device (11) comprises a plurality of conveying units (12) disposed in series and wherein a gap (14) is provided between a preceding and a subsequent conveying unit (12) which gap is associated with the monitoring device (20).

5. The discharging device (10) according to claim 4, wherein the preceding conveying unit (12) comprises at least one weighting device (15), wherein in particular a vibrating section and/or a bag pressing device (16) in the shape of e.g. a flattening and/or pressing section is provided.

6. The discharging device (10) according to claim 4, wherein at least one conveying unit (12) comprises a conveyor belt (18).

7. The discharging device (10) according to claim 1, wherein the weight sensor (21) comprises at least one strain measuring tape or a piezoelectric element.

8. The discharging device (10) according to claim 2, wherein the collecting unit (25) is configured to be rotatable or pivotable.

9. The discharging device (10) according to claim 1, wherein the monitoring device (20) comprises a collecting hopper (28).

10. The discharging device (10) according to claim 1, wherein the monitoring device (20) comprises a baffle plate (27).

11. A packaging machine (1) for filling bulk goods (29) into bags (4), comprising at least one filling element (3) by means of which a bag (4) to be filled is filled, and comprising a bag take-off device for taking off the filled bags (4) and for transferring said bags (4) to a discharging device (10), which discharging device (10) comprises a conveying device (11) for conveying off the bags (4) filled with bulk goods (29), wherein at least one monitoring device (20) is provided for monitoring the tightness of the filled bags (4) which is associated with the conveying device (11), characterized in that the monitoring device (20) comprises a weight sensor (21) which directly captures any bulk goods (29) escaping from a bag (4) to determine a parameter for the bag leakiness.

12. The packaging machine (1) according to claim 11, comprising at least one bag closing unit.

13. The packaging machine (1) according to claim 11, wherein at least one closing parameter is adapted in dependence on the parameter.

14. A method for filling bulk goods (29) into bags (4), in which a bag (4) is filled with bulk goods (29) and then closed, the filled bag (4) being transferred to a discharging device (10), wherein any bulk goods (29) escaping from the bag (4) are collected and weighed at least in part, whereupon a parameter for the bag tightness of the bag (4) is determined.

15. A method for filling bulk goods (29) into bags (4), in which a bag (4) is filled with bulk goods (29) and then closed, the filled bag (4) being transferred to a discharging device (10), wherein any bulk goods (29) escaping from the bag (4) are transferred to a baffle plate (27) at least in part and the impact momentum is captured, whereupon a parameter for the bag tightness of the bag (4) is determined.

* * * * *